(12) United States Patent
Potluri et al.

(10) Patent No.: US 8,080,668 B2
(45) Date of Patent: Dec. 20, 2011

(54) THIAZOLES DERIVATIVES AS AMPK ACTIVATOR

(75) Inventors: Vijay Kumar Potluri, Hyderabad (IN); Saibal Kumar Das, Hyderabad (IN); Pradip Kumar Sasmal, Hyderabad (IN); Javed Iqbal, Hyderabad (IN); Parimal Misra, Hyderabad (IN); Ranjan Chakrabarti, Hyderabad (IN); Rashmi Talwar, Hyderabad (IN)

(73) Assignees: Dr. Reddy's Laboratories Limited, Hyderabad, Andhra Pradesh (IN); Dr. Reddy's Laboratories, Inc., Bridgewater, NJ (US)

( * ) Notice: Subject to any disclaimer, the term of this patent is extended or adjusted under 35 U.S.C. 154(b) by 246 days.

(21) Appl. No.: 11/480,032

(22) Filed: Jun. 30, 2006

(65) Prior Publication Data

US 2007/0015665 A1  Jan. 18, 2007

(30) Foreign Application Priority Data

Jul. 4, 2005  (IN) .............................. 870/CHE/2005

(51) Int. Cl.
- *A61K 31/426* (2006.01)
- *C07D 277/38* (2006.01)
- *C07D 277/56* (2006.01)

(52) U.S. Cl. ...................... 548/194; 514/370
(58) Field of Classification Search ............ 548/194
See application file for complete search history.

(56) References Cited

U.S. PATENT DOCUMENTS

| | | | | |
|---|---|---|---|---|
| 4,025,528 A | * | 5/1977 | Maeda et al. | 548/186 |
| 4,785,008 A | * | 11/1988 | Coquelet et al. | 514/342 |
| 6,177,454 B1 | | 1/2001 | Maruyama et al. | |
| 7,645,778 B2 | * | 1/2010 | Sutton et al. | 514/342 |
| 2005/0038068 A1 | | 2/2005 | Iyengar et al. | |

FOREIGN PATENT DOCUMENTS

| WO | WO 2005058887 A1 | 6/2005 |
|---|---|---|
| WO | WO 2006058905 A1 | 6/2006 |

OTHER PUBLICATIONS

Souillac, et al., Characterization of Delivery Systems, Differential Scanning Calorimetry in Encyclopedia of Controlled Drug Delivery, 1999, John Wiley & Sons, pp. 212-227.*
Vippagunta et al., Advanced Drug Delivery Reviews, 48 (2001), pp. 3-26.*
Chemical Abstract Registry No. 885859-91-6, entry date into the Registry file on STN is May 28, 2006.*
Chemical Abstract Registry No. 725710-27-0, entry date into the Registry file on STN is Aug. 12, 2004.*
Chemical Abstract Registry No. 525572-23-0, entry date into the Registry file on STN is Jun. 5, 2003.*
Search Report and Written Opinion for PCT/US2006/025898 dated Nov. 27, 2006.
M.M. Baddi, et al., "Synthesis and Biological Activity of Some Ethyl 2- arylaminothiazole-4-carboxylates and corresponding 2-arylaminothiazole-4- carboxylic acids", Abstract; *Indian Journal of Heterocyclic Chemistry*, 1995, 4 (3), pp. 183-186, Dharwad, India.
Search Report and Written Opinion for EP 1907369 dated Jun. 18, 2009.
European Patent Office, Communication pursuant to Article 94(3) EPC, dated Jul. 30, 2010, European Patent Application No. 06774435.9-2101/1907369, Applicant Dr. Reddy's Laboratories Ltd., et al.

* cited by examiner

*Primary Examiner* — Laura L. Stockton
(74) *Attorney, Agent, or Firm* — Balaram Gupta; Robert A. Franks; Thomas C. McKenzie

(57) ABSTRACT

The present application provides novel thiazole derivatives that are useful as activators of Adenosine 5'-Monophosphate-Activated Protein Kinase and pharmaceutical compositions containing such compounds.

17 Claims, No Drawings

THIAZOLES DERIVATIVES AS AMPK ACTIVATOR

CROSS-REFERENCE TO RELATED APPLICATIONS

This application claims priority to Indian Application No. 870/CHE/2005 filed, Jul. 04, 2005.

FIELD

The present application provides novel thiazole derivatives that are Adenosine 5'-Monophosphate-Activated Protein Kinase activators and pharmaceutical compositions containing such compounds.

BACKGROUND

Adenosine 5'-Monophosphate-Activated Protein Kinase (AMP-activated protein kinase) or (AMPK) activators are believed to play a key role in regulation of carbohydrates and fat metabolism in mammals including humans. The net effects of AMPK activation may include inhibition of hepatic gluconeogenesis, cholesterol and triglyceride synthesis in liver, enhancement in muscle glucose transport and insulin sensitivity and fatty acid oxidation in muscle and liver.

SUMMARY

In accordance with one aspect, the present application provides a thiazole derivative, of the compound having formula (I):

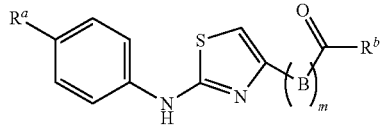

(I)

which compound is a free species and/or a pharmaceutically-acceptable salt or a solvate or a hydrate thereof, wherein $R^a$ is chosen from hydroxy, $(C_1-C_5)$ perfluoroalkyl, $(C_1-C_5)$acyl, aryl, heterocycloalkyl, heteroaryl, aryloxy, alkylaryloxy, —O—$(C_1-C_5)$alkylaryl, —S—$(C_1-C_5)$alkyl, —S—$(C_1-C_5)$perfluoroalkyl, —S-aryl or —S—$(C_1-C_5)$alkylaryl;

$R^b$ is —$OR_1$, wherein $R_1$ is hydrogen or $(C_1-C_8)$alkyl;

B is independently chosen from —$CH_2$—, —$CH(CH_3)$—, —$C(CH_3)_2$—, and —$C(CH_3)(C_2H_5)$—; and m varies between 0 and 2, inclusive.

In another aspect, the present application provides compounds having formula (II)

(II)

which compound is a free species, and/or a pharmaceutically-acceptable salt or a solvate or a hydrate thereof, wherein $R^a$ is chosen from $(C_1-C_5)$perfluoroalkyl, $(C_1-C_5)$alkyl, $(C_1-C_5)$ acyl, aryl, heterocycloalkyl, heteroaryl, aryloxy, alkylaryloxy, —S—$(C_1-C_5)$alkyl, —S—$(C_1-C_5)$perfluoroalkyl, —S-aryl or —S—$(C_1-C_5)$alkylaryl; and $R^b$ is —$OR_1$, wherein $R_1$ is hydrogen or $(C_1-C_8)$alkyl.

In accordance with another aspect, the present application also provides a thiazole derivative, of the compound having the formula (I),

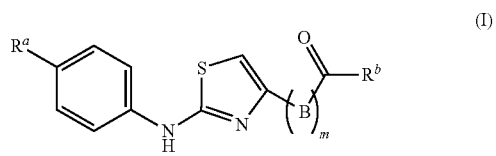

(I)

which compound is a free species and/or a pharmaceutically-acceptable salt or a solvate or a hydrate, wherein $R^a$ is chosen from fluoro, chloro, bromo, $(C_1-C_5)$ perfluoroalkyoxy, $(C_1-C_5)$alkyl, and —$XR^c$, where X is oxygen or sulfur, and $R^c$ is hydrogen, $(C_1-C_5)$alkyl, $(C1-C5)$perfluoroalkyl, aryl or $(C1-C5)$alkylaryl;

$R^b$ is —$OR_1$, wherein $R_1$ is hydrogen or $(C_1-C_8)$alkyl;

B is independently chosen from —$CH_2$, —$CH(CH_3)$—, —$C(CH_3)_2$—
and —$C(CH_3)(C_2H_5)$—; and m varies between 0 and 2, inclusive, which thiazole derivative has AMP-activated protein kinase (AMPK) potential.

Another aspect of the present application provides compounds having formula (II)

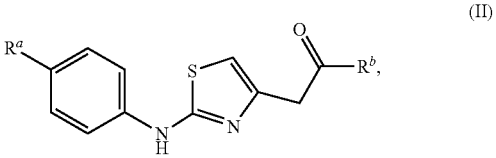

(II)

which compound is a free species, and/or a pharmaceutically-acceptable salt or a solvate or a hydrate thereof, wherein $R^a$ is chosen from $(C_1-C_5)$perfluoroalkoxy, $(C_1-C_5)$alkyl, and —$XR^c$, where X is oxygen or sulfur, and $R^c$ is hydrogen, $(C_1-C_5)$alkyl, $(C_1-C_5)$ perfluoroalkyl, aryl or $(C_1-C_5)$alkylaryl; and $R^b$ is —$OR_1$, wherein $R_1$ is hydrogen or $(C_1-C_8)$alkyl;

which thiazole derivative has AMP-activated protein kinase potential.

In accordance with another aspect of the present application provides novel thiazole derivatives of formula (I) and the formula (II) having an AMPK potential which is at least about 75%-95% in L6 skeletal muscle cells and of at least about 65%-95% in Hep G2 hepatoma liver cells. Various embodiments and variants are provided.

In accordance with another aspect, the present application provides compounds of the formula (I) and the formula (II) having an AMPK potential which is at least about 75% in L6 skeletal muscle cells and of at least about 65% in Hep G2 hepatoma liver cells.

In another aspect, the present application provides compounds of the formula (I) and the formula (II) having an AMPK potential which is at least about 85% in L6 skeletal muscle cells and of at least about 85% in Hep G2 hepatoma liver cells.

In accordance with another aspect, the present application provides compounds of the formula (I) and the formula (II)

having an AMPK potential which is at least about 90% in L6 skeletal muscle cells and of at least about 90% in Hep G2 hepatoma liver cells.

Another aspect of the present application provides compounds of formula (III),

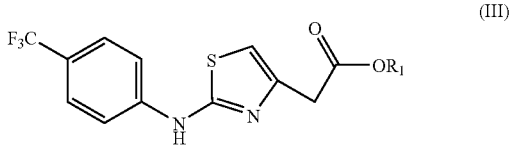

wherein $R_1$ is hydrogen or $(C_1-C_3)$alkyl.

Another aspect of the present application provides compounds of formula (I), wherein $R^a$ is thiazolyl having the structure

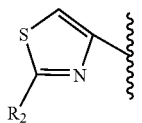

wherein $R_2$ is chosen from halogen, $(C_1-C_5)$perfluoroalkyl, $(C_1-C_5)$alkyl, $(C_1-C_5)$alkylaryl, aryl, haloaryl and $(C_1-C_5)$perfluoroalkylaryl.

In accordance with other aspects, the present application also provides a method of activating AMP-activated protein kinase (AMPK) in human or animal subject, and pharmaceutical compositions comprising one or more thiazole derivatives of the present application and one or more pharmaceutically-acceptable excipients.

In yet another aspect, the present application provides pharmaceutical compositions comprising one or more thiazole derivatives of the present application and one or more pharmaceutically-acceptable excipients.

DETAILED DESCRIPTION

To describe the application, certain terms are defined herein as follows.

The term "compound" is used to denote a molecule of unique, identifiable chemical structure. A compound may exist as a free species. Also, the free species form of the compound may form various salts, usually with external acids or bases.

The term "derivative" is used as a common term for the free species form of the compound and all its salts. Thus, the claim language "a derivative, which is a free species and/or a salt of the compound of the formula [I]" is used to define a genus comprising the free species compounds of the given formula and all the salts of the compounds of the given formula. The use of the term "and/or" is intended to indicate that, for a compound of a given chemical structure, a claim to a "derivative" covers the free species form and all of its salts, as well as the mixtures of free species and the salt forms. The term "pharmaceutically-acceptable salts" is intended to denote salts that are suitable for use in human or animal pharmaceutical products. The use of the term "pharmaceutically-acceptable" is not intended to limit the claims to substances ("derivatives") found only outside of the body.

In describing the compounds, certain nomenclature and terminology is used throughout to refer to various groups and substituents. The description "$C_x$-$C_y$," refers to a chain of carbon atoms or a carbocyclic skeleton containing from x to y atoms, inclusive. The designated range of carbon atoms may refer independently to the number of carbon atoms in the chain or the cyclic skeleton, or to the portion of a larger substituent in which the chain or the skeleton is included. For example, the recitation "$(C_1-C_5)$alkyl" refers to an alkyl group having a carbon chain of 1 to 5 carbon atoms, inclusive of 1 and 5. The chains of carbon atoms of the groups and substituents described and claimed herein may be saturated or unsaturated, straight chain or branched, substituted or unsubstituted.

The term "alkyl," whether used alone or as a part of another group, refers to a group or a substituent that includes a chain of carbon atoms. The chains of carbon atoms of the alkyl groups described and claimed herein may be saturated or unsaturated, straight chain or branched, substituted or unsubstituted. In a non-limiting example, "$C_1-C_5$ alkyl" denotes an alkyl group having carbon chain with from 1 to 5 carbon atoms, inclusive, which carbon may be saturated or unsaturated, straight chain or branched, substituted or unsubstituted. The term "perfluoroalkyl" is used to denote an alkyl group in which all hydrogen atoms had been replaced with fluorine atoms, as for example in trifluoromethyl.

The term "aryl", whether used alone or as part of a substituent group, denotes a carbocyclic aromatic radical derived from an aromatic hydrocarbon. Non-limiting examples of an "aryl" radical include phenyl, naphthyl, diphenyl, fluorophenyl, methoxyethylphenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, tolyl, xylyl, and dimethylcarbamylphenyl. The "aryl" groups of the compounds described herein may be substituted by independent replacement of 1 to 3 of the hydrogen atoms on the carbocyclic aromatic skeleton with substituents including, but not limited to, halogen, —OH, —CN, mercapto, nitro, amino, substituted amino, $(C_1-C_6)$alkyl, $(C_1-C_6)$alkoxy, $(C_1-C_6)$alkylthio, $(C_1-C_6)$alkylamino, halogenated $(C_1-C_6)$alkyl, formyl, $(C_1-C_6)$acyl, $(C_1-C_6)$alkoxyacyl, and $(C_1-C_6)$acylamido, $(C_1-C_5)$perfluoroalkyl, $(C_1-C_5)$perfluoroalkoxy.

The term "heteroaryl", whether used alone or as part of a substituent group, is used to denote a cyclic aromatic radical having from five to ten ring atoms of which at least one ring atom is a heteroatom, i.e., it is not a carbon atom. An Example is where there are from 1 to 4 heteroatoms in the ring structure selected from S, O, and N. The radical may be joined to the rest of the molecule via any of the ring atoms. Non-limiting examples of "heteroaryl" groups include pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl. The heteroaryl groups of the compounds described and/or claimed herein may be substituted by independent replacement of 1 to 3 hydrogen atoms of the aromatic skeleton with substituents including, but not limited to halogen, —OH, —CN, mercapto, nitro, amino, substituted amino, $(C_1-C_6)$alkyl, $(C_1-C_6)$alkoxy, $(C_1-C_6)$alkylthio, $(C_1-C_6)$alkylamino, halogenated $(C_1-C_6)$alkyl, formyl, $(C_1-C_6)$ acyl, (C$_1$-C$_6$)alkoxyacyl, (C$_1$-C$_6$)acylamido, aryl, (C$_1$-C$_5$) alkylaryl, (C$_1$-C$_5$)perfluoroalkyl, (C$_1$-C$_5$) perfluoroalkylaryl, and haloaryl.

The term "haloaryl" is used to denote a group comprised of an aryl group substituted with halogen atom, where aryl group is as defined above and halogen is used to denote fluorine, chlorine, bromine or iodine, an example of such group is chlorophenyl. Halogen atom on aryl ring can present on ortho, meta or para position of the ring.

The term "perfluoroalkylaryl" is used to denote a group comprised of an aryl group substituted with perfluoroalkyl group, where aryl and perfluoroalkyl groups are as defined above. An example of such group is trifluoromethylphenyl. Perfluoro group on aryl ring can present on ortho, meta or para position of the ring.

The term "acyl" used when one or more of the terminal alkyl carbon atoms or ring carbon atoms of the aryl ring are substituted with one or more carbonyl radicals, specifically embraces monoalkylcarbonyl such as methylcarbonyl, ethylcarbonyl and the like, arylcarbonyl, such as benzoyl and the like. The term acyl also includes formyl group.

The term "alkylaryl" is used to denote a group comprised of an aryl radical and a carbon chain that connects the aryl radical to the rest of the molecule, for example benzyl group.

The term "heterocycloalkyl", whether used alone or as part of a substituent group, is used to denote a cyclic non-aromatic radical having from five to ten ring atoms of which at least one ring atom is heteroatom, i.e., it is not a carbon atom. An example is where there are from 1 to 4 heteroatoms in the ring structure selected from S, O, and N. Non-limiting examples of a heterocycloalkyl group are aziridinyl, azetidinyl, pyrrolidinyl, piperidinyl, azepinyl, piperazinyl, 1,2,3,6-tetrahydropyridinyl, oxiranyl, oxetanyl, tetrahydrofuranyl, tetrahydrothienyl, tetrahydropyranyl, tetrahydrothiopyranyl, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, quinolizinyl, quinuclidinyl, 1,4-dioxaspiro[4.5]decyl, 1,4-dioxaspiro[4.4]nonyl, 1,4-dioxaspiro[4.3]octyl, and 1,4-dioxaspiro[4.2]heptyl.

Examples of 5- or 6-membered heterocycloalkyl group formed by R$_2$ and R$_3$ are morpholine ring, thiomorpholine ring and the like.

Unless specified otherwise, it is intended that the definition of any substituent or variable at a particular location in a molecule be independent of its definitions elsewhere in that molecule. It is understood that substituents and substitution patterns on the compounds of this application can be selected by one of ordinary skill in the art to provide compounds that are chemically stable and that can be readily synthesized by techniques known in the art as well as those methods set forth herein.

A group may be referred to generally or more specifically, as desired. For example, a group containing a carbon chain with one carbon-carbon double bond may be described as alkyl or alkenyl, as desired. Another non-limiting example, a group containing a carbon chain with a chloro substituent may be described as alkyl or halogenated alkyl, as desired.

A "composition" may contain one compound or a mixture of compounds. A "pharmaceutical composition" is any composition useful or potentially useful in producing physiological response in a subject to which such pharmaceutical composition is administered. The term "pharmaceutically acceptable" with respect to excipients is used to define non-toxic substances generally suitable for use in human or animal pharmaceutical products.

The AMPK activation potential percentages in this specification are calculated with respect to the already known AMPK activator metformin. The percentages are obtained by normalizing the values obtained at concentrations in the range of 2 μM to 10 μM with that of metformin by considering the values obtained for metformin at 2 mM concentrations as 100%. However, the AMPK activation potential percentages can also be calculated with respect to other known AMPK activators also.

In accordance with one aspect, the present application provides a thiazole derivative, of the compound having formula (I):

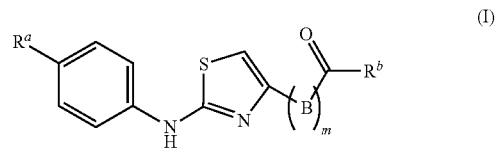

which compound is a free species and/or a pharmaceutically-acceptable salt or a solvate or a hydrate thereof, wherein $R^a$ is chosen from hydroxy, (C$_1$-C$_5$)perfluoroalkyl, (C$_1$-C$_5$)acyl, aryl, heterocycloalkyl, heteroaryl, aryloxy, alkylaryloxy, —O—(C$_1$-C$_5$)alkylaryl, —S—(C$_1$-C$_5$)alkyl, —S—(C$_1$-C$_5$) perfluoroalkyl, —S-aryl or —S—(C$_1$-C$_5$)alkylaryl;

$R^b$ is —OR$_1$, wherein R$_1$ is hydrogen or (C$_1$-C$_8$)alkyl;

B is independently chosen from —CH$_2$—, —CH(CH$_3$)—, —C(CH$_3$)$_2$—, and —C(CH$_3$)(C$_2$H$_5$)—; and m varies between 0 and 2, inclusive.

In another embodiment of the present application provides compounds having formula (II)

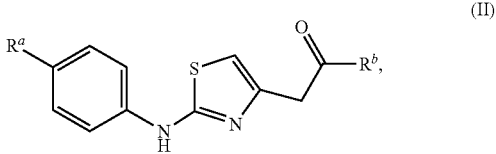

which compound is a free species, and/or a pharmaceutically-acceptable salt or a solvate or a hydrate thereof, wherein $R^a$ is chosen from (C$_1$-C$_5$)perfluoroalkyl, (C$_1$-C$_5$)alkyl, (C$_1$-C$_5$)acyl, aryl, heterocycloalkyl, heteroaryl, aryloxy, alkylaryloxy, —S—(C$_1$-C$_5$)alkyl, —S—(C$_1$-C$_5$)perfluoroalkyl, —S—aryl or —S—(C$_1$-C$_5$)alkylaryl; and $R^b$ is —OR$_1$, wherein R$_1$ is hydrogen or (C$_1$-C$_8$)alkyl.

In accordance with another aspect, the present application also provides a thiazole derivative, of the compound having the formula (I),

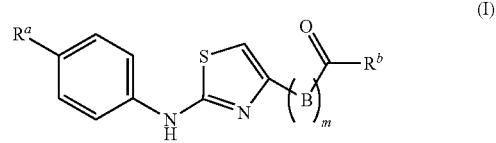

which compound is a free species and/or a pharmaceutically-acceptable salt or a solvate or a hydrate, wherein $R^a$ is chosen from fluoro, chloro, bromo, (C$_1$-C$_5$)perfluoroalkoxy, (C$_1$-C$_5$)alkyl, and —XR$^c$, where X is oxygen or sulfur, and R$^c$ is hydrogen, (C$_1$-C$_5$)alkyl, (C1-C5)perfluoroalkyl, aryl or (C1-C5)alkylaryl;

$R^b$ is —OR$_1$, wherein R$_1$ is hydrogen or (C$_1$-C$_8$)alkyl;

B is independently chosen from —CH$_2$—, —CH(CH$_3$)—, —C(CH$_3$)$_2$— and —C(CH₃)(C₂H₅)—; and m varies between 0 and 2, inclusive, which thiazole derivative has AMP-activated protein kinase (AMPK) potential.

Another aspect of the present application provides compounds having formula (II)

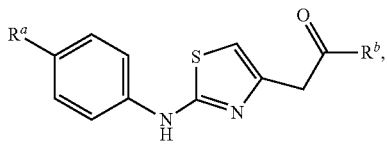

(II)

which compound is a free species, and/or a pharmaceutically-acceptable salt or a solvate or a hydrate thereof, wherein $R^a$ is chosen from $(C_1-C_5)$perfluoroalkoxy, $(C_1-C_5)$alkyl, and —$XR^c$, where X is oxygen or sulfur, and $R^c$ is hydrogen, $(C_1-C_5)$alkyl, $(C_1-C_5)$ perfluoroalkyl, aryl or $(C_1-C_5)$alkylaryl; and $R^b$ is —$OR_1$, wherein $R_1$ is hydrogen or $(C_1-C_8)$alkyl;

which thiazole derivative has AMP-activated protein kinase potential.

In accordance with another embodiment, the present application provides compounds of the formula (I) and formula (II) having an AMPK potential which is at least about 75%-95% in L6 skeletal muscle cells and of at least about 65%-95% in Hep G2 hepatoma liver cells.

In accordance with another embodiment, the present application provides compounds of the formula (I) and formula (II) having an AMPK potential which is at least about 75% in L6 skeletal muscle cells and of at least about 65% in Hep G2 hepatoma liver cells.

In accordance with another embodiment, the present application provides compounds of the formula (I) and formula (II) having an AMPK potential which is at least about 85% in L6 skeletal muscle cells and of at least about 85% in Hep G2 hepatoma liver cells.

In accordance with another embodiment, the present application provides compounds of the formula (I) and formula (II) having an AMPK potential which is at least about 90% in L6 skeletal muscle cells and of at least about 90% in Hep G2 hepatoma liver cells.

Another embodiment of the present application provides compounds of formula (II), wherein $R^a$ is $(C_1-C_5)$perfluoroalkyl.

In another embodiment the present application provides thiazole derivative of the formula (II) wherein $R^a$ is triflurom-ethyl.

Another embodiment of the present application provides compounds of formula (III),

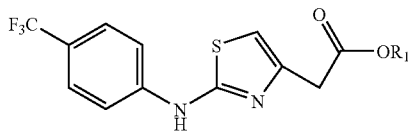

(III)

wherein $R_1$ is hydrogen or $(C_1-C_3)$alkyl.

Another embodiment of the present application provides compounds of formula (I), wherein $R^a$ thiazolyl.

Another embodiment of the provides compounds of formula (I), wherein $R^a$ is thiazolyl having the structure

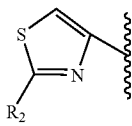

wherein $R_2$ is chosen from halogen, $(C_1-C_5)$perfluoroalkyl, $(C_1-C_5)$alkyl, $(C_1-C_5)$alkylaryl, aryl, haloaryl and $(C_1-C_5)$ perfluoroalkylaryl.

Another embodiment of the present application provides compounds of formula (I), wherein $R^a$ is a heterocycloalkyl group having the structure —$NR_3R_4$, wherein $R_3$ and $R_4$ together with the nitrogen atom of the group —$NR_3R_4$, form a 5- or 6-membered heterocycloalkyl ring which may optionally contain one or two hetero further heteroatoms selected from oxygen, sulfur or nitrogen.

Another embodiment of the present application provides compounds of formula (I), wherein said heterocycloalkyl group is morpholinyl.

Another embodiment of the present application provides the thiazole derivative of formula (I), which has the structure

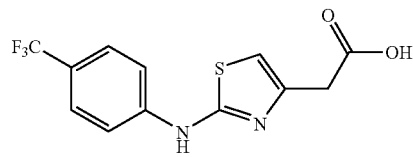

Another embodiment of the present application provides the thiazole derivative of formula (I), which has the structure

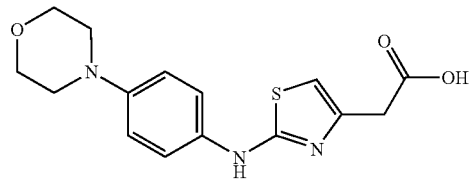

Another embodiment of the present application provides the thiazole derivative of formula (I), which has the structure

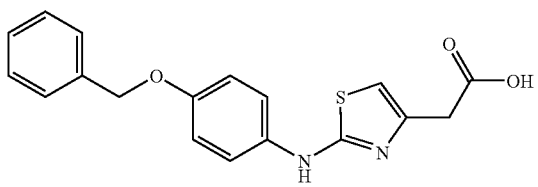

Another embodiment of the present application provides the thiazole derivative of formula (I), which has the structure

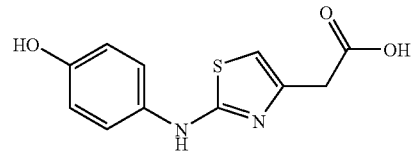

Another embodiment of the present application provides the thiazole derivative of formula (I), which has the structure

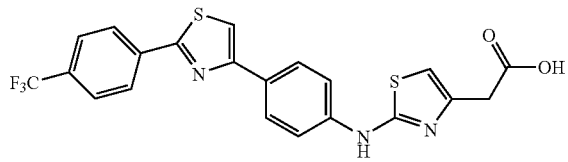

Another embodiment of the present application provides the thiazole derivative of formula (I), which has the structure

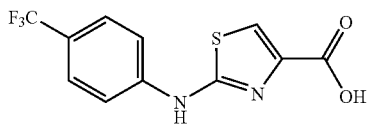

According to another embodiment of the present application provides novel thiazole derivatives of formula (I) that have AMP kinase activation potential.

According to another embodiment of the present application provides novel thiazole derivatives of formula (I) that have an AMP kinase activation potential of at least about 75%-90% in L6 skeletal muscle cells and of at least about 60%-90% in Hep G2 hepatoma liver cells, According to another embodiment, the present application provides the compound of formula (I) as defined in the above embodiment, wherein $R^a$ is $(C_1\text{-}C_5)$perfluoroalkyl.

Another embodiment of the present application provides a method of activating AMPK in human or animal subject, said method comprising administering said subject with an effective amount of the thiazole derivative of compound of formula (I).

Another embodiment of the present application provides a pharmaceutical composition comprising a therapeutically effective amount of a compound of formula (I) in combination with a pharmaceutically suitable carrier.

Another embodiment of the present application provides a pharmaceutical composition comprising one or more thiazole derivatives of compound of formula (I) and one or more pharmaceutically-acceptable excipients.

Another embodiment of the present application provides a pharmaceutical composition comprising one or more thiazole derivatives of compound of formula (II) and one or more pharmaceutically-acceptable excipients.

According to another embodiment of the present application provides a thiazole derivative, which is a free species and/or a pharmaceutically-acceptable salt of the compound of the formula (I).

Specific Examples of Formula (I) Include, but are not Limited to

| Structure | IUPAC Name |
|---|---|
| 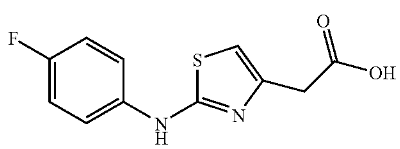 | [2-(4-Fluoro-phenylamino)-thiazol-4-yl]-acetic acid |
| 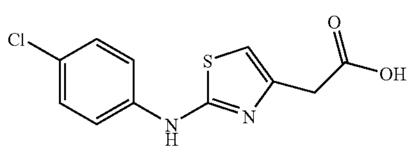 | [2-(4-Chloro-phenylamino)-thiazol-4-yl]-acetic acid |
| 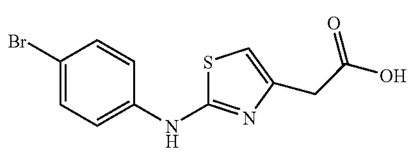 | [2-(4-Bromo-phenylamino)-thiazol-4-yl]-acetic acid |
| 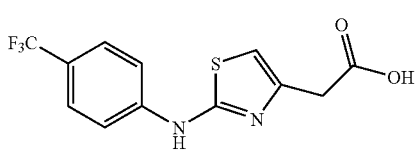 | [2-(4-Trifluoromethyl-phenylamino)-thiazol-4-yl]-acetic acid |
| 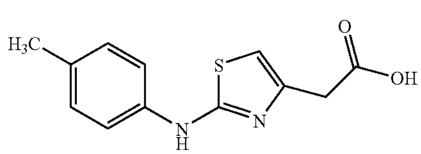 | (2-p-Tolylamino-thiazol-4-yl)-acetic acid |

| Structure | IUPAC Name |
|---|---|
| 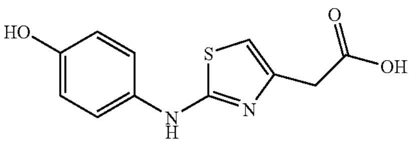 | [2-(4-Hydroxy-phenylamino)-thiazol-4-yl]-acetic acid |
| 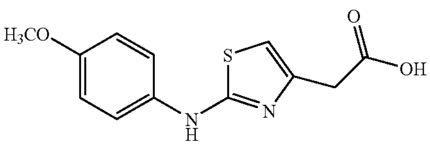 | [2-(4-Methoxy-phenylamino)-thiazol-4-yl]-acetic acid |
| 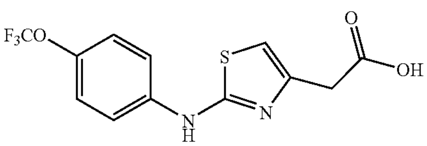 | [2-(4-Trifluoromethoxy-phenylamino)-thiazol-4-yl]-acetic acid |
| 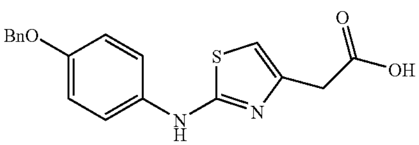 | [2-(4-Benzyloxy-phenylamino)-thiazol-4-yl]-acetic acid |
| 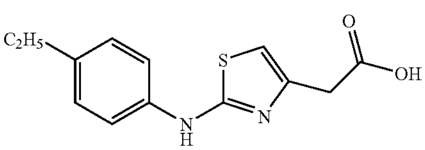 | [2-(4-Ethoxy-phenylamino)-thiazol-4-yl]-acetic acid |
| 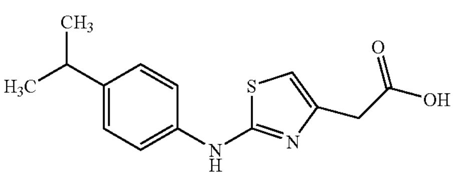 | [2-(4-Isopropoxy-phenylamino)-thiazol-4-yl]-acetic acid |
| 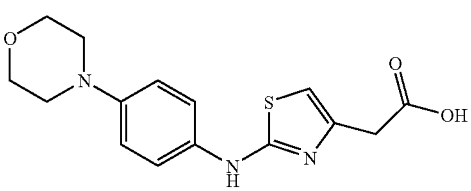 | [2-(4-Morpholin-4-yl-phenylamino)-thiazol-4-yl]-acetic acid |
| 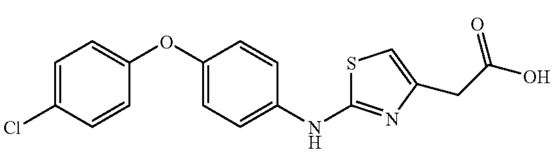 | {2-[4-(4-Chloro-phenoxy)-phenylamino]-thiazol-4-yl}-acetic acid |
| 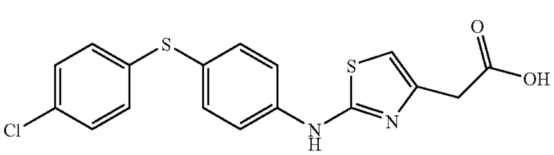 | {2-[4-(4-Chloro-phenylsulfanyl)-phenylamino]-thiazol-4-yl}-acetic acid |

-continued

| Structure | IUPAC Name |
|---|---|
| 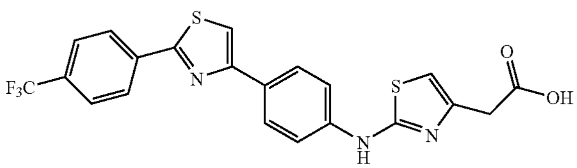 | (2-{4-[2-(4-Trifluoromethyl-phenyl)-thiazol-4-yl]-phenylamino}-thiazol-4-yl)-acetic acid |
| 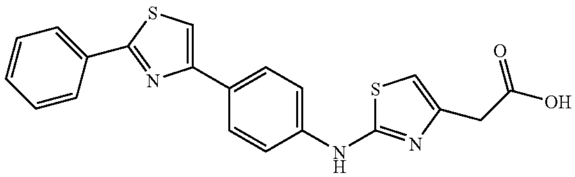 | {2-[4-(2-Phenyl-thiazol-4-yl)-phenylamino]-thiazol-4-yl}-acetic acid |
| 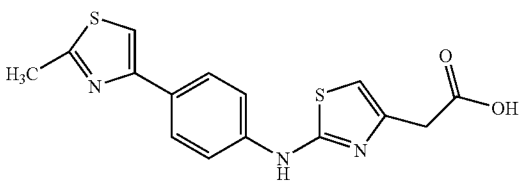 | {2-[4-(2-Methyl-thiazol-4-yl)-phenylamino]-thiazol-4-yl}-acetic acid |
| 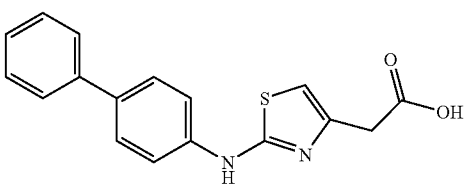 | [2-(Biphenyl-4-ylamino)-thiazol-4-yl]-acetic acid |
| 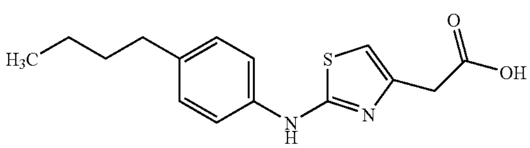 | [2-(4-Butyl-phenylamino)-thiazol-4-yl]-acetic acid |
| 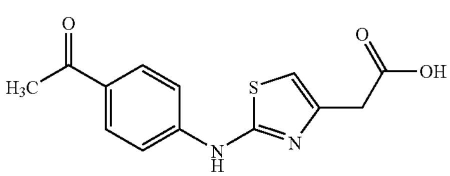 | [2-(4-Acetyl-phenylamino)-thiazol-4-yl]-acetic acid |
| 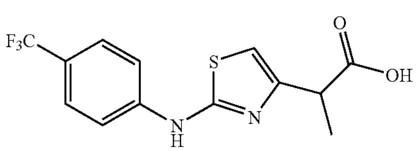 | 2-[2-(4-Trifluoromethyl-phenylamino)-thiazol-4-yl]-propionic acid |
| 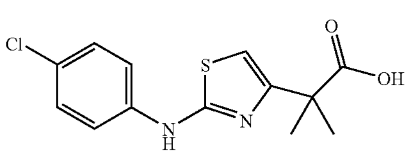 | 2-[2-(4-Chloro-phenylamino)-thiazol-4-yl]-2-methyl-propionic acid |
| 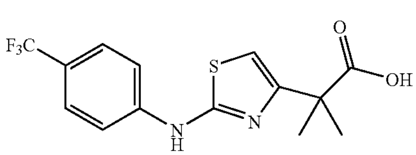 | 2-Methyl-2-[2-(4-trifluoromethyl-phenylamino)-thiazol-4-yl]-propionic acid |

-continued

| Structure | IUPAC Name |
|---|---|
| 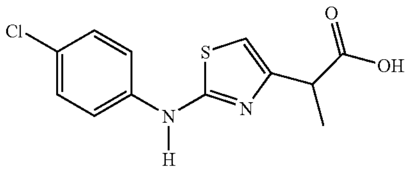 | 2-[2-(4-Chloro-phenylamino)-thiazol-4-yl]-propionic acid |
| 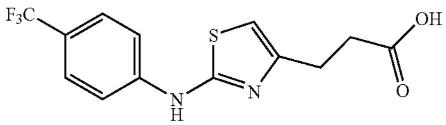 | 3-[2-(4-Trifluoromethyl-phenylamino)-thiazol-4-yl]-propionic acid |
| 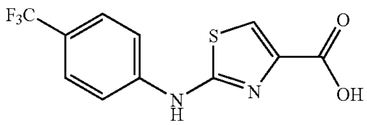 | 2-(4-Trifluoromethyl-phenylamino)-thiazole-4-carboxylic acid |
| 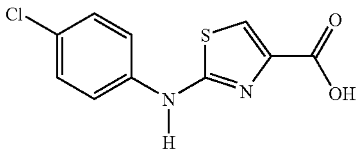 | 2-(4-Chloro-phenylamino)-thiazole-4-carboxylic acid |
| 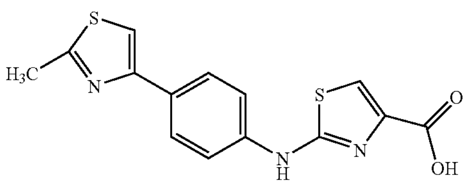 | 2-[4-(2-Methyl-thiazol-4-yl)-phenylamino]-thiazole-4-carboxylic acid |
| 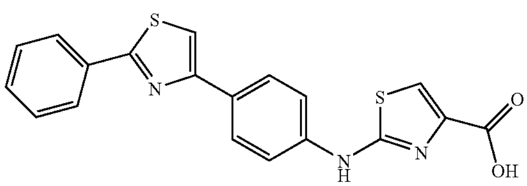 | 2-[4-(2-Phenyl-thiazol-4-yl)-phenylamino]-thiazole-4-carboxylic acid |
| 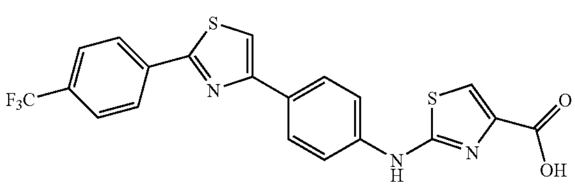 | 2-{4-[2-(4-Trifluoromethyl-phenyl)-thiazol-4-yl]-phenylamino}-thiazole-4-carboxylic acid |

Compounds of formula (I) may be prepared in the manner shown in the following preparation schemes or by any other known means.

Compounds of (I) thus prepared may be isolated and purified from the reaction mixture by known means, including but not limited to, solvent extraction, concentration, neutralization, filtration, crystallization, recrystallization, column chromatography, high performance liquid chromatography and recrystallization, to give a highly purified product of interest.

The compounds of the present application and salts thereof can be prepared by applying various synthetic methods utilizing the characteristics due to the fundamental skeleton or type of the substituents thereof. Representative production methods will be illustrated as hereunder. All other symbols are as defined earlier.

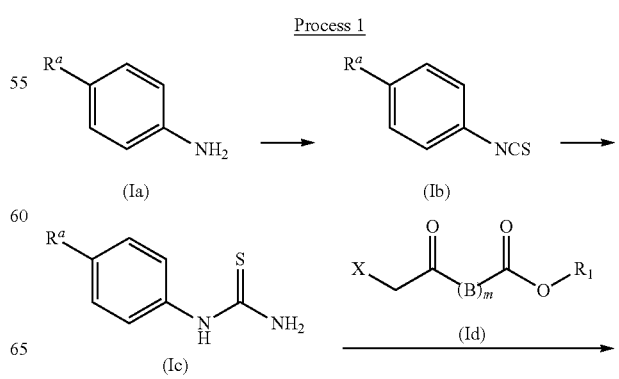

Process 1

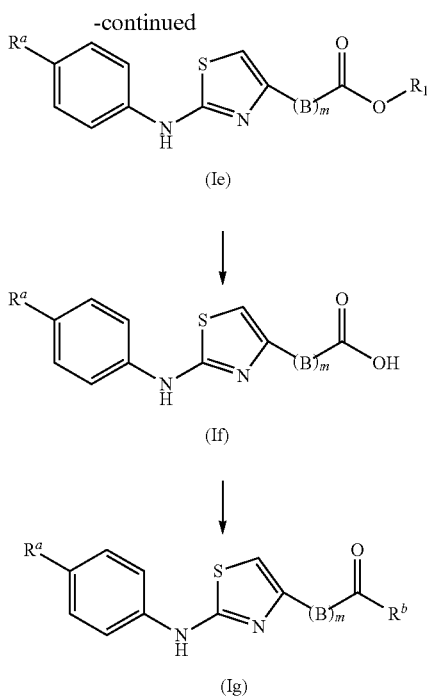

(Ie)

(If)

(Ig)

The compound of formula (Ia) was converted to a compound of formula (Ib) in presence of thiophosgene, pyridine and solvent, where all symbols are as defined earlier. The solvent used in the reaction can be selected from dichloromethane, dichloroethane, pyridine, chloroform, tetrachloromethane, ethylacetate, methanol, ethanol, isopropanol, n-propanol, butanol, acetone, acetonitrile, dimethylformamide, dimethylsulfoxide, tetrahydrofuran, water and the like or a mixture thereof. The reaction can be carried out at a temperature between about −10° C. to about 45° C. The duration of reaction can be maintained for a period in the range of about 5 minutes to about 3 hours, for instance about 30 minutes.

The compound of formula (Ib) was converted to a compound of formula (Ic) in presence of ammonia or aqueous ammonia solution and solvent, where all symbols are as defined earlier. The solvent used in the reaction can be selected from dichloromethane, dichloroethane, pyridine, chloroform, tetrachloromethane, ethylacetate, methanol, ethanol, isopropanol, n-propanol, butanol, acetone, acetonitrile, dimethylformamide, dimethylsulfoxide, tetrahydrofuran, water and the like or a mixture thereof. The reaction can be carried out at a temperature between about 10° C. to about 65° C. The duration of reaction can be maintained for a period in the range of about 1 hour to about 10 hours, for instance about 6 hours.

Compound of the formula (Ie) was obtained by reacting the compound of formula (Ic) with the compound of formula (Id) in presence of solvent, wherein X represents a leaving group such as halogen atom, p-toluenesulfonate, methanesulfonate, trifluoromethane sulfonate or the like, $R_1$ is selected from alkyl having 1 to 5 carbon atoms, where non-limiting examples include, methyl, ethyl, n-propyl, iso-propyl or n-butyl, and the other symbols are as defined earlier. The solvent used in the reaction can be selected from dichloromethane, dichloroethane, pyridine, chloroform, tetrachloromethane, ethylacetate, methanol, ethanol, isopropanol, n-propanol, butanol, acetone, acetonitrile, dimethylformamide, dimethylsulfoxide, tetrahydrofuran, water and the like or a mixture thereof. The reaction can be carried out at a temperature between about 40° C. to about 150° C. The duration of reaction can be maintained for a period in the range of about 6 hour to about 18 hours, for instance about 12 hours.

Hydrolysis of compound of formula (Ie) gave compound of formula (If), where all symbols are as defined earlier. The solvent used in the reaction can be selected from dichloromethane, dichloroethane, pyridine, chloroform, tetrachloromethane, ethylacetate, methanol, ethanol, isopropanol, n-propanol, butanol, acetone, acetonitrile, dimethylformamide, dimethylsulfoxide, tetrahydrofuran, water and the like or a mixture thereof. The hydrolysis can be carried out in presence of acid or base for example, in the presence of base such as sodium hydroxide, potassium hydroxide, sodium carbonate, potassium carbonate and the like. The reaction can be carried out at a temperature between about 25° C. to about 75° C. The duration of reaction can be maintained for a period in the range of about 25 minutes to about 3 hours, for instance about 45 minutes.

The compound of formula (If) was converted to compound of formula (Ig) in presence of $NH_2$—$R^c$, where all symbols are as defined earlier. The solvent used in the reaction can be selected from dichloromethane, dichloroethane, pyridine, chloroform, tetrachloromethane, ethylacetate, methanol, ethanol, isopropanol, n-propanol, butanol, acetone, acetonitrile, dimethylformamide, dimethylsulfoxide, tetrahydrofuran, water and the like or a mixture thereof. The reaction can be carried out at a temperature between about 25° C. to about 75° C. The duration of reaction can be maintained for a period in the range of about 1 hour to about 5 hours, for instance about 2 hours.

Process 2

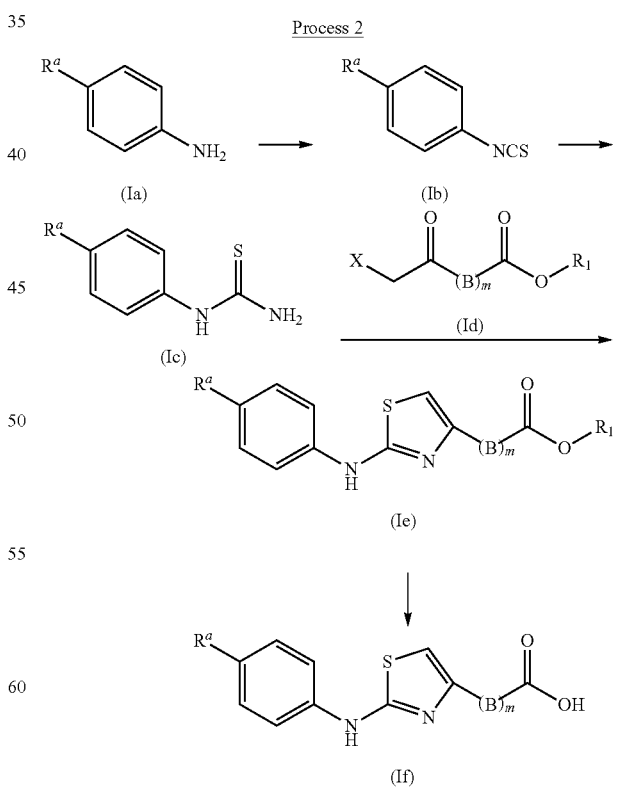

The compound of formula (Ia) was converted to a compound of formula (Ib) in presence of thiophosgene and pyridine, where all symbols are as defined earlier. The solvent used in the reaction can be selected from dichloromethane, dichloroethane, pyridine, chloroform, tetrachloromethane, ethylacetate, methanol, ethanol, isopropanol, n-propanol, butanol, acetone, acetonitrile, dimethylformamide, dimethylsulfoxide, tetrahydrofuran, water and the like or a mixture thereof. The reaction can be carried out at a temperature between about −10° C. to about 45° C. The duration of reaction can be maintained for a period in the range of about 5 minutes to about 2 hours, for instance about 30 minutes.

The compound of formula (Ib) was converted to a compound of formula (Ic) in presence of ammonia or aqueous ammonia solution, where all symbols are as defined earlier. The solvent used in the reaction can be selected from dichloromethane, dichloroethane, pyridine, chloroform, tetrachloromethane, ethylacetate, methanol, ethanol, isopropanol, n-propanol, butanol, acetone, acetonitrile, dimethylformamide, dimethylsulfoxide, tetrahydrofuran, water and the like or a mixture thereof. The reaction can be carried out at a temperature between about 10° C. to about 45° C. The duration of reaction can be maintained for a period in the range of about 1 hour to about 10 hours, for instance about 6 hours.

Compound of formula (Ie) was obtained by reacting the compound of formula (Ic) with the compound of formula (Id), wherein X represents a leaving group such as halogen atom, p-toluenesulfonate, methanesulfonate, trifluoromethane sulfonate or the like, $R_1$ is selected from alkyl having 1 to 5 carbon atoms, where non-limiting examples include methyl, ethyl, n-propyl, iso-propyl or n-butyl, and the other symbols are as defined earlier. The solvent used in the reaction can be selected from dichloromethane, dichloroethane, pyridine, chloroform, tetrachloromethane, ethylacetate, methanol, ethanol, isopropanol, n-propanol, butanol, acetone, acetonitrile, dimethylformamide, dimethylsulfoxide, tetrahydrofuran, water and the like or a mixture thereof. The reaction can be carried out at a temperature between about 10° C. to about 45° C. The duration of reaction can be maintained for a period in the range of about 1 hour to about 10 hours, for instance about 6 hours.

Hydrolysis of compound of formula (Ie) gave compound of formula (If), where all symbols are as defined earlier. The solvent used in the reaction can be selected from dichloromethane, dichloroethane, pyridine, chloroform, tetrachloromethane, ethylacetate, methanol, ethanol, isopropanol, n-propanol, butanol, acetone, acetonitrile, dimethylformamide, dimethylsulfoxide, tetrahydrofuran, water and the like or a mixture thereof. The hydrolysis can be carried out in presence of acid or base for example in presence of base such as sodium hydroxide, potassium hydroxide and the like. The reaction can be carried out at a temperature between about 25° C. to about 65° C. The duration of reaction can be maintained for a period in the range of about 25 minutes to about 2 hours, for instance about 45 minutes.

Process 3

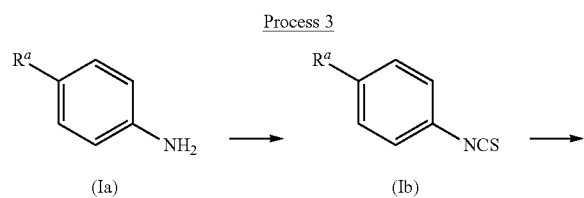

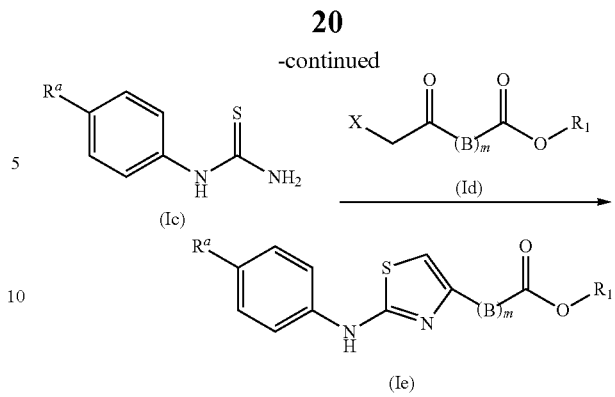

The compound of formula (Ia) was converted to a compound of formula (Ib) in presence of thiophosgene and pyridine, where all symbols are as defined earlier. The solvent used in the reaction can be selected from dichloromethane, dichloroethane, pyridine, chloroform, tetrachloromethane, ethylacetate, methanol, ethanol, isopropanol, n-propanol, butanol, acetone, acetonitrile, dimethylformamide, dimethylsulfoxide, tetrahydrofuran, water and the like or a mixture thereof. The reaction can be carried out at a temperature between about −10° C. to about 45° C. The duration of reaction can be maintained for a period in the range of about 5 minutes to about 2 hours, for instance about 30 minutes.

The compound of formula (Ib) was converted to a compound of formula (Ic) in presence of ammonia or aqueous ammonia solution, where all symbols are as defined earlier. The solvent used in the reaction can be selected from dichloromethane, dichloroethane, pyridine, chloroform, tetrachloromethane, ethylacetate, methanol, ethanol, isopropanol, n-propanol, butanol, acetone, acetonitrile, dimethylformamide, dimethylsulfoxide, tetrahydrofuran, water and the like or a mixture thereof. The reaction can be carried out at a temperature between about 10° C. to about 45° C. The duration of reaction can be maintained for a period in the range of about 1 hour to about 10 hours, for instance about 6 hours.

Compound of the formula (Ie) was obtained by reacting the compound of formula (Ic) with the compound of formula (Id), wherein X represents a leaving group such as halogen atom, p-toluenesulfonate, methanesulfonate, trifluoromethane sulfonate or the like , $R_1$ is selected from alkyl having 1 to 5 carbon atoms, where non-limiting examples include methyl, ethyl, n-propyl, iso-propyl or n-butyl, and the other symbols are as defined earlier. The solvent used in the reaction can be selected from dichloromethane, dichloroethane, pyridine, chloroform, tetrachloromethane, ethylacetate, methanol, ethanol, isopropanol, n-propanol, butanol, acetone, acetonitrile, dimethylformamide, dimethylsulfoxide, tetrahydrofuran, water and the like or a mixture thereof. The reaction can be carried out at a temperature between about 10° C. to about 45° C. The duration of reaction can be maintained for a period in the range of about 1 hour to about 10 hours, for instance about 6 hours.

The following Examples and Experimental procedures are merely illustrative, and compounds of the present application are not limited by the following embodiments in any case. A person skilled in the art can implement the present application at maximum by variously altering, not only in the following Examples but also in the claims of the present specification, and such alterations are included in claims of the present specification.

EXAMPLE -1

Synthesis of [2-(4-Trifluoromethyl-phenylamino)-thiazol-4-yl]-acetic acid

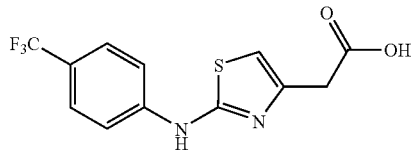

Step (i): Preparation of 1-Isothiocyanato-4-trifluoromethyl-benzene

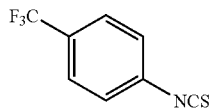

Thiophosgene (5 mL) was added portion wise to a stirred solution of 4-trifluoromethyl-phenylamine (10 grams) and pyridine (12.5 mL) in dichloromethane (2 Liters) at 0° C. The reaction was maintained at the same temperature for 30 minutes. The reaction mixture was then diluted with dichloromethane and washed several times with a saturated solution of copper sulfate, followed by water, drying over sodium sulfate and evaporating to give the crude product which was further purified by passing through a column of silica gel, to yield the pure product (11 grams).
Melting point: 45-47° C.
MS: 204 (M$^+$+1); $^1$H NMR (CDC$_{13}$): 7.62 (d, J=7.6 Hz, 2H), 7.32 (d, J=7.6 Hz, 2H); IR (cm$^{-1}$): 3442, 2925, 2099, 1654, 1327, 1126, 1067.

Step (ii): Preparation of (4-Trifluoromethyl-phenyl)thiourea

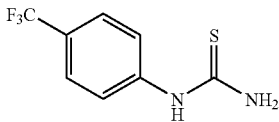

A solution of 1-isothiocyanato-4-trifluoromethyl-benzene (5 grams), obtained in step (i), in acetone (10 mL) was added to stirred aqueous ammonia (100 mL). The solution was stirred at about 25-35° C. for about 6 hours. The solid obtained was filtered and dried and used for further reactions.
Meling point: 136-139° C.
MS: 221 (M$^+$+1); $^1$H NMR (DMSO-d$_6$) 10.03 (s, 1H), 7.78 (br m, 6H); IR (cm$^{-1}$): 3458, 3282, 3184, 1628, 1524, 1325, 1122.

Step (iii): Preparation of [2-(4-Trifluoromethyl-phenylamino)-thiazol-4-yl]-acetic acid ethyl ester

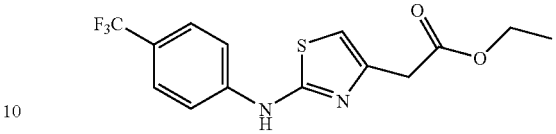

4-Chloro-3-oxo-butyric acid ethyl ester was added to a suspension of (4-trifluoromethyl-phenyl)-thiourea (3 grams), obtained in step (ii), in ethanol (20 mL) and refluxed for about 12 hrs. The reaction mixture was cooled and the solid obtained was filtered and dried to give the pure product (4.1 grams).
Meling point: 172-175° C.
MS: 331 (M$^+$+1); $^1$H NMR (DMSO-d$_6$) 10.85 (br, 1H), 7.81 (d, J=8.8 Hz), 6.64 (d, J=8.8 Hz, 1H), 6.80, (s, 1H), 4.11 (q, J=7.2 Hz, 2H), 3.68 (s, 2H), 1.21 (t, J=7.2 Hz, 3H); IR (cm$^{-1}$): 3442, 2924, 1730, 1608, 1569, 1327, 1196, 1131.

Step (iv): Preparation of [2-(4-Trifluoromethyl-phenylamino)-thiazol-4-yl]-acetic acid

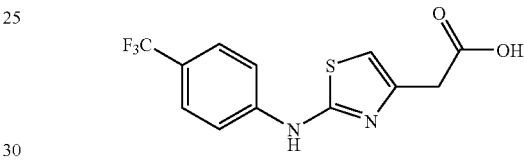

[2-(4-trifluoromethyl-phenylamino)-thiazol-4-yl]-acetic acid ethyl ester (4 grams), obtained in step (iii), was dissolved in minimum ethanol and 10 % sodium hydroxide (30 mL) was added and stirred at about 25-35° C. for about 45 minutes. The reaction mixture was then diluted with water and neutralized with saturated aqueous citric acid. The solid that precipitated was filtered washed with water and dried to give the product (3.2 grams).
Meling point: 169-171° C.
MS: 303(M$^+$+1), 259 (M+—CO$_2$); $^1$H NMR (DMSO-d$_6$): 12.33 (br, 1H), 10.56 (br, 1H), 7.78 (d, J=8.4 Hz, 2H), 7.64 (d, J=8.4 Hz, 2H), 6.76 (s, 1H), 3.59 (s, 1H); IR (cm$^{-1}$): 3001, 1687, 1435.

The compounds of Examples 1-a to 1-r, given in the below Table 1 were prepared according to the manner as described in Example 1:

TABLE 1

The example given in the below table were obtained by defining various groups/values for R$^a$, R$^b$, B and m in the below general formula:

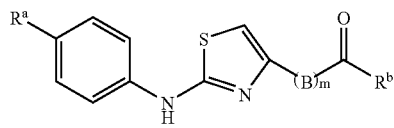

| Ex | R$^a$ | B | m | R$^b$ | Data |
|---|---|---|---|---|---|
| 1-a | —F | —CH$_2$— | 1 | —OH | Melting point: 138-140° C. MS: 208 (M$^+$ − CO$_2$). $^1$H NMR (DMSO-d$_6$): 12.5 (br, 1H), 10.13 (br, 1H), 7.61 (m, 2H), 7.13 (m, 2H), 6.62 (s, 1H), 3.53 (s, 2H) IR (cm$^{-1}$): 3382, 2925, 1683 |

TABLE 1-continued

The example given in the below table were obtained by defining various groups/values for $R^a$, $R^b$, B and m in the below general formula:

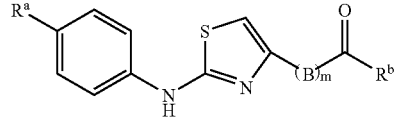

| Ex | $R^a$ | B | m | $R^b$ | Data |
|---|---|---|---|---|---|
| 1-b | —Cl | —CH$_2$— | 1 | —OH | Melting point: 166-168° C. MS: 224 (M$^+$ − CO$_2$). $^1$H NMR (DMSO-d$_6$): 12.31 (br, 1H), 10.27 (br, 1H), 7.63 (d, J = 9.2 Hz, 2H), 7.33 (d, J = 9.2 Hz, 2H), 6.67 (s, 1h), 3.55 (s, 2H). IR (cm$^{-1}$): 3420, 1684, 1433. |
| 1-c | —Br | —CH$_2$— | 1 | —OH | Melting point: 168-170° C. MS: 313 (M$^+$), 271 (M$^+$ − CO$_2$). $^1$H NMR: DMSO-d$_6$ 12.31 (br, 1H), 10.27 (br, 1H), 7.57, (d, J = 2.4 Hz, 1H), 7.45 (d, J = 8.8 hz, 2H), 6.67 (s, 1H), 3.55 (s, 2H). IR (cm$^{-1}$): 2992, 1684, 1561, 1491. |
| 1-d | —CH$_3$ | —CH$_2$— | 1 | —OH | Melting point: 154-156° C. MS: 248 (M$^+$). $^1$H NMR (DMSO-d$_6$): 12.27 (br, 1H), 9.99 (br, 1H), 7.45 (d, J = 8.4 Hz, 2H), 7.09 (d, J = 8.4 Hz, 2H), 6.58 (s, 1H), 3.52 (s, 2H), 2.24 (s, 3H). IR (cm$^{-1}$): 3251, 3128, 1694, 1218. |
| 1-e | —OCF$_3$ | —CH$_2$— | 1 | —OH | Melting point: 137-139° C. MS: 319 (M$^+$ + 1). $^1$H NMR (DMSO-d$_6$): 12.31 (br, 1H), 10.33 (br, 1H), 7.71 (m, 2H), 7.69 (m, 2H), 6.69 (s, 1H), 3.56 (s, 2H). IR (cm$^{-1}$): 3445, 1682, 1501, 1046. |
| 1-f | (benzyloxymethyl group) | —CH$_2$— | 1 | —OH | Melting point: 116-118° C. MS: 341 (M$^+$ + 1). $^1$H NMR (DMSO-d$_6$): 12.20 (br, 1H), 9.90 (br, 1H), 7.3-7.5 9m, 7H), 6.94 (d, J = 8.8 Hz, 2H), 6.54 (s, 1H), 5.05 (s, 2H), 350 (s, 2H). IR (cm$^{-1}$): 3447, 3300, 1629, 1244. |
| 1-g | —C$_2$H$_5$ | —CH$_2$— | 1 | —OH | Melting point: 150-151° C. MS: 263 (M$^+$ + 1). $^1$H NMR (DMSO-d$_6$): 12.33 (br, 1H), 10.03 (br, 1H), 7.47 (d, J = 8.6 Hz, 2H), 7.07 (d, J = 8.6 Hz, 2H), 6.59 (s, 1H), 3.52 (s, 2H), 2.52 (m 2H), 1.15 (t, J = 6.6 Hz, 3H). IR (cm$^{-1}$): 3252, 3127, 1694, 1312, 830. |
| 1-h | -i-Pr | —CH$_2$— | 1 | —OH | Melting point: 127-129° C. MS: 227 (M$^+$ − CO$_2$). $^1$H NMR (DMSO-d$_6$): 12.32 (br, 1H), 10.04 (br, 1H), 7.47 (d, J = 8.6 Hz, 2H), 7.16 (d, J = 8.6 Hz, 2H), 6.59 (s, 1H), 3.52 (s, 2H), 2.82 (m, 1H), 1.18 (d, J = 6.8 Hz, 6H). IR (cm$^{-1}$): 3424, 2960, 1611, 1438, 817. |

TABLE 1-continued

The example given in the below table were obtained by defining various groups/values for $R^a$, $R^b$, B and m in the below general formula:

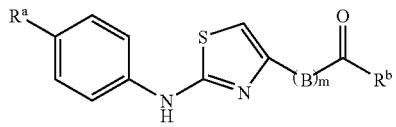

| Ex | $R^a$ | B | m | $R^b$ | Data |
|---|---|---|---|---|---|
| 1-i | 4-methylmorpholinyl | —CH$_2$— | 1 | —OH | Melting point: 198-199° C.<br>MS: 320 (M$^+$ + 1), 276 (M$^+$ + 1 − CO$_2$).<br>$^1$H NMR (DMSO-d$_6$): 12.45 (br, 1H), 9.83 (br, 1H), 7.42 (d, J = 9.2 Hz, 2H), 6.95 (d, J = 9.2 Hz, 2H), 6.52 (s, 1H), 3.73 (s, 4H), 3.49 (s, 2H), 3.02 (m, 2H).<br>IR (cm$^{-1}$): 3296, 3121, 1685, 1534. |
| 1-j | 4-chloro-methylthiophenyl | —CH$_2$— | 1 | —OH | Melting point: 191-192° C.<br>MS: 377 (M$^+$), 332.9 (M$^+$ − CO$_2$).<br>$^1$H NMR (DMSO-d$_6$): 12.31 (br, 1H), 10.39 (br, 1H), 7.69 (d, J = 8.4 Hz, 2H), 7.43 (d, J = 8.4 Hz, 2H), 7.35 (d, J = 8.4 Hz, 2H), 7.13 (d, J = 8.4 Hz, 2H), 6.71 (s, 1H), 3.56 (s, 2H).<br>IR (cm$^{-1}$): 3449, 3247, 1694, 1549. |
| 1-k | 4-chloro-methoxyphenyl | —CH$_2$— | 1 | —OH | Melting point: 192-193° C.<br>MS: 361 (M$^+$), 316.9 (M$^+$ − CO$_2$).<br>$^1$H NMR (DMSO-d$_6$) 12.28 (br, 1H), 10.16 (br, 1H), 7.63 (d, J = 8.8 Hz, 2H), 7.38 (d, J = 9.2 Hz, 2H), 7.03 (d, J = 8.8 Hz, 2H), 6.96 (d, J = 8.8 Hz, 2H), 6.62 (s, 1H), 3.53 (s, 2H).<br>IR (cm$^{-1}$): 3438, 3064, 1693, 1506. |
| 1-l | 4-methyl-2-(4-trifluoromethylphenyl)thiazolyl | —CH$_2$— | 1 | —OH | Melting point: 171-174° C.<br>MS: 462 (M$^+$ + 1), 416 (M$^+$ + 1 − CO$_2$).<br>$^1$H NMR (DMSO-d$_6$): 10.3 (br, 1H), 8.24 (d, J= 8 Hz, 2H), 8.1 (s, 1H), 8.0 (d, J = 8.8 Hz, 2H), 7.9 (d, J = 8.3 Hz, 2H), 7.7 (d, J = 8.8 Hz, 2H), 6.7 (s, 1H), 3.5 (s, 2H). |
| 1-m | 4-methyl-2-phenylthiazolyl | —CH$_2$— | 1 | —OH | Melting point: 148-150° C.<br>MS: 394 (M$^+$ + 1).<br>$^1$H NMR (DMSO-d$_6$): 10.3 (br, 1H), 8.0 (m, 5H), 7.72 (d, J = 7.2 Hz, 2H), 7.63 (m, 3H), 6.7 (s, 1H0, 3.6 (s, 2H).<br>IR (cm$^{-1}$): 3257, 3111, 1707, 1480. |

TABLE 1-continued

The example given in the below table were obtained by defining various groups/values for $R^a$, $R^b$, B and m in the below general formula:

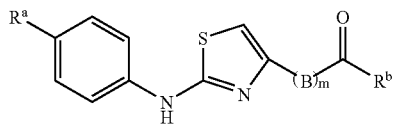

| Ex | $R^a$ | B | m | $R^b$ | Data |
|---|---|---|---|---|---|
| 1-n | 4,2-dimethylthiazol-5-yl | —CH$_2$— | 1 | —OH | Melting point: 153-156° C.<br>MS: 332 (M$^+$ + 1).<br>$^1$H NMR (DMSO-d$_6$): 12.31 (br, 1H), 10.25 (br, 1H), 7.85 (d, J = 8.8 Hz, 2H), 7.73 (s, 1H), 7.63 (d, J = 8.8 Hz, 2H), 6.67 (s, 1H), 3.56 (s, 2H), 2.70 (s, 3H).<br>IR (cm$^{-1}$): 3265, 3070, 1687, 1611. |
| 1-o | 4-methylphenyl | —CH$_2$— | 1 | —OH | Melting point: 158-159° C.<br>MS: 311 (M+ + 1). 297.5<br>$^1$H NMR (DMSO-d$_6$) 12.33 (br, 1H), 10.26 (br, 1H), 7.61-7.69 (m, 6H), 7.41-7.48 (m, 2H), 7.28-7.32 (m, 1H), 6.66 (s, 1H), 3.56 (s, 2H)<br>IR (cm$^{-1}$): 3250, 3124, 1692, 1522. |
| 1-p | —C$_4$H$_9$ | —CH$_2$— | 1 | —OH | Melting point: 136-139° C.<br>MS: 291 (M$^+$ + 1).<br>$^1$H NMR (DMSO-d$_6$): 12.2 (br, 1H), 10 (br, 1H), 7.45 (d, J = 8.5 Hz, 2H), 7.09 (d, J = 8.3 Hz, 2H), 6.6 (s, 1H), 3.5 (s, 2H), 2.5 (t, J = 7.5 Hz, 2H), 1.5-1.56 (m, 2H), 1.34 (q, J = 7.5 Hz, 2H), 0.9 (t, J = 7.5 Hz, 3H).<br>IR (cm$^{-1}$): 3263, 2929, 1892, 1692, 1617 |
| 1-q | —C(=O)—CH$_3$ | —CH$_2$— | 1 | —OH | Melting point: 166-168° C.<br>MS: 233 (M+ − CO2)<br>$^1$H NMR (DMSO-d$_6$): d$_6$ 12.40 (br, 1H), 10.61 (br, 1H), 7.93 (d, J = 8.8 Hz, 2H), 6.71 (d, J = 8.8 Hz, 2H), 6.78 (s, 1H), 3.60 (s, 2H), 2.51 (s, 3H)<br>IR (cm$^{-1}$): 2922, 1668, 1599, 1355, 1247, 1185. |
| 1-r | —OCH$_3$ | —CH$_2$— | 1 | —OH | Melting point: 149-151° C.<br>MS: 221 (M$^+$ + 1 − CO$_2$)<br>$^1$H NMR (DMSO-d$_6$): 12.26 (br, 1H), 9.88 (br, 1H), 7.48 (d, J = 8.8 Hz, 2H), 6.89 (d, J = 8.4 Hz, 2H), 6.54 (s, 1H), 3.71 (s, 3H), 3.50 (s, 2H).<br>IR (cm$^{-1}$): 3422, 2926, 1637, 1513, 1026. |

EXAMPLE-(1-s)

[2-(4-Hydroxy-phenylamino)-thiazol-4-yl]-acetic acid

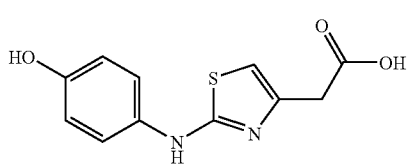

[2-(4-Benzyloxy-phenylamino)-thiazol-4-yl]-acetic acid (1.0 gram), obtained in example-1-f, was dissolved in trifluoro acetic acid (5 mL) and refluxed for about 1 hour. Trifluoro acetic acid was removed in vacuo and the product was crystallized from ethanol.

Melting point: 150-152° C.

MS: 251 (M$^+$+1)

$^1$H NMR (DMSO-d$_6$): 12.40 (br, 1H), 9.79 (br, 1H), 9.09 (br, 1H), 7.33 9d, J=8.8 Hz, 2H), 6.71 (d, J=8.4 Hz, 2H), 6.51 (s, 1H), 3.49 (s, 2H).

IR (cm$^{-1}$): 3114, 2750, 1629, 1370.

EXAMPLE-2

Preparation of 2-(4-Trifluoromethyl-phenylamino)-thiazole-4-carboxylic acid

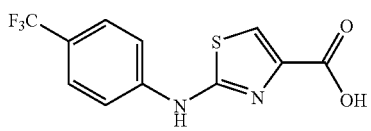

3-Bromo-2-oxo-propionic acid ethyl ester (0.59 mL) was added to a suspension of (4-trifluoromethyl-phenyl)-thiourea (1 grams), obtained in step (ii) of example-1, in ethanol (20 mL) and refluxed for about 12 hours. The reaction mixture was cooled and the solid obtained was filtered and dissolved in a minimum amount ethanol. 10% sodium hydroxide solution (10 mL) was added and stirred at about 25-35° C. for about 12 hours. The reaction mixture was then diluted with water and acidified with saturated citric acid solution. The solid that precipitated was filtered washed with water and dried to give the product (0.65 grams).

Melting point: 255-259° C.

MS: 288 (M+); $^1$H NMR (DMSO-$d_6$) 12.3 (br, 1H), 10.8 (s, 1H), 7.9-7.8 (m, 3H) 7.7-7.6 (m, 2H);

IR (cm$^{-1}$): 3442, 1722, 1331.

The compounds of Examples 2-a to 2-d, given in the below Table 2 were prepared according to the manner as described in Example 2:

TABLE 2

The example given in the below table were obtained by defining various groups/values for $R^a$, $R^b$ and m in the below general formula:

| Ex | $R^a$ | m | $R^b$ | Data |
|---|---|---|---|---|
| 2-a | —Cl | 0 | —OH | Melting point: 287° C. MS: 255 (M+). $^1$H NMR (DMSO-$d_6$): 12.51 (br, 1H), 10.28 (br, 1H), 7.68 (d, J = 8.8 Hz, 2H), 7.59 (s, 1H), 7.27 (d, J = 8.8 Hz, 2H). IR (cm$^{-1}$): 3384, 3127, 1675. |
| 2-b | 2,4-dimethylthiazol-5-yl | 0 | —OH | Melting point: 290-292° C. MS: 317 (M+). $^1$H NMR (DMSO-$d_6$): 12.71 (br, 1H), 10.45 (br, 1H), 7.89 (d, J = 8.8 Hz, 2H), 7.88 (s, 1H), 7.72 (m, 2H), 2.71 (s, 3H). IR (cm$^{-1}$): 2985, 1709, 1613, 1441. |
| 2-c | 4-methyl-2-phenyl-thiazol-5-yl | 0 | —OH | Melting point: 283-286° C. MS: 380 (M+). $^1$H NMR (DMSO-$d_6$): 12.6 (br, 1H), 10.5 (b, 1H), 8.0 (t, J = 4.8 Hz, 5H), 7.8-7.7 (m, 3H), 7.6-7.4 (m, 3H). IR (cm$^{-1}$): 2924, 1610, 1481, 762. |
| 2-d | 4-methyl-2-(4-trifluoromethylphenyl)-thiazol-5-yl | 0 | —OH | Melting point: 280-283° C. MS: 477 (M+). $^1$H NMR (DMSO-$d_6$): 10.5 (s, 1H), 8.24 (d, J = 8,2 Hz, 2H), 8.15 (s, 1H), 8.07 (d, J = 8.5 Hz, 2H), 7.9 (m, 2H), 7.84 (m, 3H). IR (cm$^{-1}$): 3987, 1677, 1325, 1167. |

The compounds of Examples 3-a to 3-e, given in the below Table 3 were prepared according to the manner as described in Example 1, by utilizing the appropriate 5 starting material.

TABLE 3

The example given in the below table were obtained by defining various groups/values for $R^a$, $R^b$, B and m in the below general formula:

| Ex | $R^a$ | B | m | $R^b$ | Data |
|---|---|---|---|---|---|
| 3-a | —CF$_3$ | —CH(CH$_3$)— | 1 | —OH | Melting point: 124-126° C. MS: 315 M+ − 1), 273 (M+ − CO2) $^1$H NMR (DMSO-$d_6$): $d_6$ 12.28 (br, 1H), 10.57 (br, 1H), 7.77 (d, J = 8.8 Hz, 2H), 7.63 (d, J = 8.8 Hz, 2H), 6.73 (s, 1H), 3.71 (q, J = 6.8 Hz, 1H), 1.22 (d, J = 6.8 Hz, 3H) |
| 3-b | —Cl | —C(CH$_3$)$_2$ | 1 | —OH | Melting point: 140-142° C. MS: 253 (M+ + 1) $^1$H NMR (DMSO-$d_6$): 11..99 (br, 1H), 10.26 (s, 1H), 7.63 (d, J = 8.4 Hz, 2H), 7.32 (d, J = 8.4 Hz, 2H), 6.63 (s, 1H), 1.46 (s, 6H) IR (cm$^{-1}$): 3420, 2925, 1611, 1493 |

TABLE 3-continued

The example given in the below table were obtained by defining various groups/values for $R^a$, $R^b$, B and m in the below general formula:

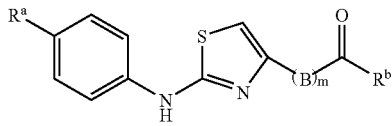

| Ex | $R^a$ | B | m | $R^b$ | Data |
|---|---|---|---|---|---|
| 3-c | —CF$_3$ | —C(CH$_3$)$_2$ | 1 | —OH | Melting point: 158-159° C. <br> $^1$H NMR (DMSO-d$_6$): 12.32 (br, 1H), 10.53 (s, 1H), 7.82 (d, J = 8.4 Hz, 2H), 7.65 (d, J = 8.4 Hz, 1H), 6.72 (s, 1H), 1.48 (s, 6H) <br> IR (cm$^{-1}$): 3426, 2925, 1605, 1010. |
| 3-d | —Cl | —OH(CH$_3$)— | 1 | —OH | Melting point: 133-135° C. <br> MS: 283 (M+) <br> $^1$H NMR (DMSO-d$_6$): 12.23 (br, 1H), 10.28 (s, 1H), 7.62 (d, J = 8.4 Hz, 2H), 7.32 (d, J = 8.4 Hz, 1H), 6.34 (s, 1H), 3.68 (q, J = 6.8 Hz, 1H), 1.39 (d, J = 6.8 Hz, 3H) <br> IR (cm$^{-1}$): 3380, 1598, 1492, 1432, 1024. |
| 3-e | —CF$_3$ | —CH$_2$— | 2 | —OH | Melting point: 191-193° C. <br> $^1$H NMR (DMSO-d$_6$): 12.12 (br, 1H), 10.52 (s, 1H), 7.81 (d, J = 8.8 Hz, 2H), 6 <br> IR (cm$^1$): 2925, 1692, 1620, 1330, 1069. |

Symbols in the tables have the following meanings:
Ex means Example number;
Data means physicochemical properties;
NMR is nucleomagnetic resonance spectrum;
MS is mass spectra;
IR is infrared spectroscopy;
iPr is isopropyl.

Pharmaceutically acceptable salts of the present application includes salts with inorganic bases, salts with organic bases, salts with inorganic acids, salts with organic acids, and salts with basic or acidic amino acids.

Examples of salts with inorganic bases include but are not limited to, alkali metal salts such as sodium salt and potassium salt, alkaline earth metal salts such as calcium salt and magnesium salt, as well as aluminum salt and ammonium salt. Examples of salts with organic bases include those which are formed with trimethylamine, triethylamine, pyridine, picoline, ethanolamine, diethanolamine, triethanolamine, dicyclohexylamine and N,N'-dibenzyl-ethylenediamine. Examples of salts with inorganic acids include but are not limited to, those which are formed with hydrochloric acid, hydrobromic acid, nitric acid, sulfuric acid and phosphoric acid. Examples of salts with organic acids include those which are formed with formic acid, acetic acid, trifluoroacetic acid, fumaric acid, oxalic acid, tartaric acid, maleic acid, citric acid, succinic acid, malic acid, methanesulfonic acid, benzenesulfonic acid and p-toluenesulfonic acid. Examples of salts with basic amino acids include those which are formed with arginine, lysine and ornithine. Ideal examples of salts with acidic amino acids include those which are formed with aspartic acid and glutamic acid.

A prodrug of the compound of formula (I) refers to a compound capable of converting into the compound of formula (I) by the action of enzymes, gastric acid and the like under in vivo physiological conditions. Specifically, a compound capable of converting into the compound of formula (I) through, for example, (a) enzymatic oxidation, reduction and/or hydrolysis or (b) hydrolysis by gastric acid.

Examples of a prodrug of the compound of formula (I) include:

(A) compounds obtained when an amino group of the compound of formula (I) is acylated, alkylated or phosphorylated, such as those obtained when an amino group of the compound of formula (I) is eicosanoylated, alanylated, pentylaminocarbonylated, (5-methyl-2-oxo-1,3-dioxolen-4-yl)methoxycarbonylated, tetrahydro-furanylated, tetrahydropyranylated, pyrrolidylmethylated, pivaloyloxymethylated or tert-butylated;

(B) compounds obtained when a hydroxy group of the compound of formula (I) is acylated, alkylated, phosphorylated or borated, such as those obtained when a hydroxy group of the compound of formula (I) is acetylated, palmitoylated, propanoylated, pivaloylated, succinylated, fumalylated, alanylated, dimethylaminomethylcarbonylated or tetrahydro-pyranylated; and (C) compounds obtained when a carboxyl group of the compound of formula (I) is esterified or amidated, such as those obtained when a carboxyl group of the compound of formula (I) is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified or methylamidated. These compounds may be prepared from the compound of formula (I) in a known manner.

The compounds of the present application are useful as activators of AMP kinase. The AMPK system is the probable target for known antidiabetic compounds like metformin. Increased recruitment of the AMPK signaling system either by excessive or pharmaceutical activators may have beneficial effects. The in vivo activation of AMPK is expected to have profound beneficial effects. It is expected that in liver, decreased expression of gluconeogenic enzymes would reduce hepatic glucose output and improve the overall glucose homeostasis. Further, both direct inhibition and/or reduced expression of key enzymes in lipid metabolism is expected to lead to decreased fatty acid and cholesterol synthesis and increased fatty acid oxidation. Stimulation of AMPK in skeletal muscle is expected to increase glucose uptake and fatty acid oxidation, resulting in improvement of glucose homeostasis. It is also expected that due to a reduction in intra-myocyte triglyceride accumulation, stimulation would lead to improved insulin action.

AMPK activation potential of the compounds of formula (I) was evaluated using a cell based ELISA approach. L6 muscle skeletal muscle and Hep G2 hepatoma liver cells were cultured for 48 hours prior to drug addition at various concentrations. Twenty four hours later, the cells were fixed and the ELISA plate developed following standard protocol using p-AMPK specific antibody.

ELISA Test:

Various cell lines such as HepG2 and L6 were revived from glycerol stocks (ATCC). The cells were maintained in a T 75 culture flask-containing medium (DMEM +10% fetal calf serum). On reaching a confluence of 70% to 80%, the cells were seeded in a 96 well plate at a density of $10 \times 10^3$ cells per well in DMEM +10% FCS medium. The plates were then incubated at 37° C. with 5% CO$_2$ for 48 hours. Various concentrations of drugs were prepared in DMSO and diluted to required concentration with the medium and incubated at 37° C. with 5% CO$_2$ for 24 hours. Cells were fixed with 4% formaldehyde in PBS for 30 minutes at 25-35° C. and washed three times with PBS containing 0.1% Triton X-100. Endogenous peroxidase was quenched with 0.6% $H_2O_2$ in PBS-T for 30 minutes and washed three times in PBS-T. The cells were then blocked with 10% FCS in PBS-T for 1hour. The cells were incubated for 8-12 hours with various concentrations of primary antibody in PBS-T containing 5% BSA at 4° C., followed by washing three times with PBS-T for 5 minutes and incubating with a secondary antibody (HRP conjugated 1:500 in PBS-T with 5% BSA for 1 hour at 25-35° C. The cells were washed three times with PBS-T for 5 minutes and twice with PBS and incubated with 100 µl TMB/$H_2O_2$ color developing solution for 15 minutes. The reaction was stopped with 50 µl of 1M $H_2SO_4$. The plate was then read at 460 nM using ELISA plate reader.

AMPK activation percentages for various compounds are given in the table below (AMPK activation potential percentages are obtained by normalizing the values obtained at 10 µM concentration with that of metformin by considering the values obtained for metformin at 2 mM concentrations as 100%).

| | AMPK % activation (at 10 µM) | |
|---|---|---|
| Example No. | L6 skeletal muscle cells | HepG-2 hepatoma muscle cells |
| 1-a | 81 | 97.9 |
| 1-b | 102.63 | 87.11 |
| 1-d | 99.55 | 97.11 |
| 1-f | 88.04 | 87.76 |
| 1-e | 94.09 | 100.29 |
| 1-g | 87.83 | 128.37 |
| 1-h | 75.65 | 102.15 |
| 1-i | 109.09 | 69.71 |
| 1-j | 97.09 | 97.56 |
| 1-k | 96.19 | 97.56 |
| 1-l | 104.37 | 85.27 |
| 1-n | 83.62 | 98.42 |
| 1-p | 102.26 | 75.77 |
| 1-s | 92.35 | 86.08 |
| 2-a | 94.90 | 97.26 |
| 2-c | 102.19 | 96.35 |
| 2-d | 109.70 | 83.89 |
| 3-e | 94.72 | 110.47 |

The pharmaceutical compositions of the present application may be prepared by admixture and are suitably adapted for oral, parenteral or topical administration, and as such may be in the form of tablets, capsules, oral liquid preparations, powders, granules, lozenges, pastilles, reconstitutable powders, injectable and infusible solutions or suspensions, suppositories and transdermal devices.

Solvates of the thiazole derivatives of the present may be prepared by conventional methods such as dissolving the thiazole derivative in solvents such as water, methanol, ethanol and the like.

Hydrates of the thiazole derivatives of the present require the presence of water at some stage; water may be added as a co-solvent in the process. However, it is also possible to provide sufficient water for hydrate formation by carrying out the reaction with exposure to atmospheric moisture, or by use of non-anhydrous solvents.

Tablets and capsules for oral administration are usually presented in a unit dose, and contain conventional excipients such as binding agents, fillers, diluents, tableting agents, lubricants, disintegrants, colorants, flavorings, and wetting agents. The tablets may be coated according to methods known in the art.

Suitable fillers for use include cellulose, mannitol, lactose and other similar agents. Suitable disintegrants include starch, polyvinylpyrrolidone and starch derivatives such as sodium starch glycolate. Suitable lubricants include, for example, magnesium stearate. Suitable pharmaceutically acceptable wetting agents include sodium lauryl toluenesulfonate.

Solid oral compositions may be prepared by conventional methods such as blending, filling, tableting and the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminum stearate gel or hydrogenated edible fats; emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid; and if desired conventional flavoring or coloring agents.

For parenteral administration, fluid unit dose forms are prepared containing a compound of the present application and a sterile vehicle. The compound, depending on the vehicle and the concentration, can be either suspended or dissolved. Parenteral solutions are normally prepared by dissolving the active compound in a vehicle and filter sterilizing before filling into a suitable vial or ampoule and sealing. Advantageously, adjuvants such as a local anesthetic, preservatives and buffering agents may also dissolved in the vehicle. To enhance the stability, the composition can be frozen after filling into the vial and the water removed under vacuum.

Parenteral suspensions are prepared in substantially the same manner except that the active compound is suspended in the vehicle instead of being dissolved and sterilized by exposure to ethylene oxide before suspending in the sterile vehicle. Advantageously, a surfactant or wetting agent is included in the composition to facilitate uniform distribution of the active compound.

What is claimed is:

1. A compound of the formula (I):

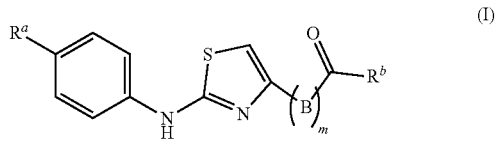

or a pharmaceutically-acceptable salt thereof; wherein $R^a$ is chosen from hydroxy, $C_1$-$C_5$acyl, or heterocycloalkyl;

$R^b$ is $OR_1$ wherein $R_1$ is hydrogen;

B is independently chosen from —$CH_2$—, —$CH(CH_3)$—, —$C(CH_3)_2$— and —$C(CH_3)(C_2H_5)$—; and m varies between 0 and 2, inclusive.

2. The compound of claim 1, which is of the formula (II):

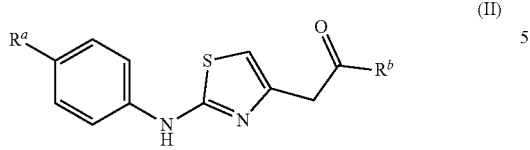

(II)

or a pharmaceutically-acceptable salt thereof, wherein
$R^a$ is chosen from hydroxy, $(C_1\text{-}C_5)$acyl, or heterocycloalkyl; and
$R^b$ is —$OR_1$, wherein $R_1$ is hydrogen.

3. The compound of claim 1, wherein $R^a$ is heterocycloalkyl having the structure —$NR_3R_4$, wherein $R_3$ and $R_4$, together with the nitrogen atom of the group —$NR_3R_4$, form a 5- or 6-memebered heterocycloalkyl group.

4. The compound of claim 3, wherein said heterocycloalkyl group is morpholinyl.

5. The compound of claim 1, which has the structure:

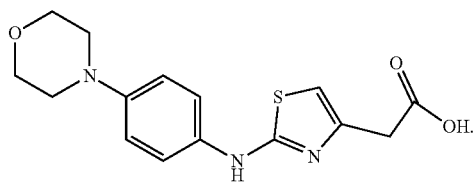

6. The compound of claim 1, which has the structure:

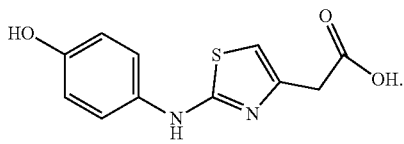

7. A compound of the formula:

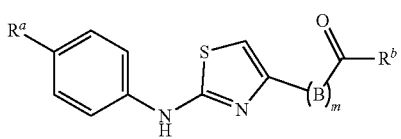

(I)

or a pharmaceutically-acceptable salt thereof, wherein
$R^a$ is chosen from hydroxy, $(C_1\text{-}C_5)$acyl, or heterocycloalkyl;
$R^b$ is —$OR_1$ wherein $R_1$ is hydrogen;

B is independently chosen from —$CH_2$, $CH(CH_3)$—, —$C(CH_3)_2$—, and —$C(CH_3)(C_2H_5)$; and
m varies between 0 and 2, inclusive;
which compound has AMP-activated protein kinase activity of at least about 75%-95% in L6 skeletal muscle cells and at least about 5%-95% in Hep-G2 hepatoma-muscle cells as determined by assaying in a cell based immuno assay.

8. The compound of claim 7, wherein said AMP-activated protein kinase activity is at least about 85% in L6 skeletal muscle cells and of at least about 85% in Hep G2 hepatoma liver cells.

9. The compound of claim 7, wherein said AMP-activated protein kinase activity is at least about 90% in L6 skeletal muscle cells and of at least about 90% in Hep G2 hepatoma liver cells.

10. The compound of claim 7, wherein said compound has the formula (II):

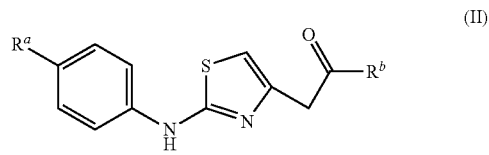

(II)

wherein $R^a$ is chosen from hydroxy, $(C_1\text{-}C_5)$acyl, or heterocycloalkyl; and
$R^b$ is —$OR_1$, wherein $R_1$ is hydrogen.

11. The compound of claim 10, wherein said AMP-activated protein kinase activity is at least about 75% in L6 skeletal muscle cells and of at least about 65% in Hep G2 hepatoma liver cells.

12. The compound of claim 10, wherein said AMP-activated protein kinase activity is at least about 85% in L6 skeletal muscle cells and of at least about 85% in Hep G2 hepatoma liver cells.

13. The compound of claim 10, wherein said AMP-activated protein kinase activity is at least about 90% in L6 skeletal muscle cells and of at least about 90% in Hep G2 hepatoma liver cells.

14. A pharmaceutical composition comprising one or more compounds of claim 1 and one or more pharmaceutically-acceptable excipients.

15. A pharmaceutical composition comprising one or more compounds of claim 2 and one or more pharmaceutically-acceptable excipients.

16. A pharmaceutical composition comprising one or more compounds of claim 7 and one or more pharmaceutically acceptable excipients.

17. A pharmaceutical composition comprising one or more compounds of claim 10 and one or more pharmaceutically acceptable excipients.

* * * * *